United States Patent [19]

Maki

[11] 4,252,159
[45] Feb. 24, 1981

[54] DOSAGE DEVICE

[76] Inventor: Eugene B. Maki, 1319 E. Hennepin Ave., Minneapolis, Minn. 55414

[21] Appl. No.: 25,763

[22] Filed: Apr. 2, 1979

[51] Int. Cl.³ ............................................. B65B 3/32
[52] U.S. Cl. ................................ 141/27; 128/218 C;
141/95; 141/375; 222/44; 222/309
[58] Field of Search ............. 128/215, 218 C; 141/2,
141/25, 26, 27, 94, 95, 375; 222/43, 44, 309

[56] References Cited

U.S. PATENT DOCUMENTS

| | | | |
|---|---|---|---|
| 2,771,217 | 11/1956 | Brown et al. | 222/43 |
| 3,833,030 | 9/1974 | Waldbauer et al. | 141/26 |
| 3,844,318 | 10/1974 | Raia | 141/27 |

*Primary Examiner*—Frederick R. Schmidt

*Attorney, Agent, or Firm*—Merchant, Gould, Smith, Edell, Welter & Schmidt

[57] ABSTRACT

A dosage device 2 or 102 which includes a body 20 on which a syringe 4 and a container of medication 6 may be mounted. An adjustable stop member 42 or 142 is located in back of the plunger 12 of syringe 4. The dosage level can be changed by varying the position of the stop member. In addition, the dosage device includes structure for indicating the position of the stop member relative to the body to a visually impaired or blind person. This position indicating structure is effective whenever the stop member moves through one of a plurality of discrete positions to allow the blind person to change the dosage level of the syringe by sensing and counting the indications generated by the position indicator.

3 Claims, 6 Drawing Figures

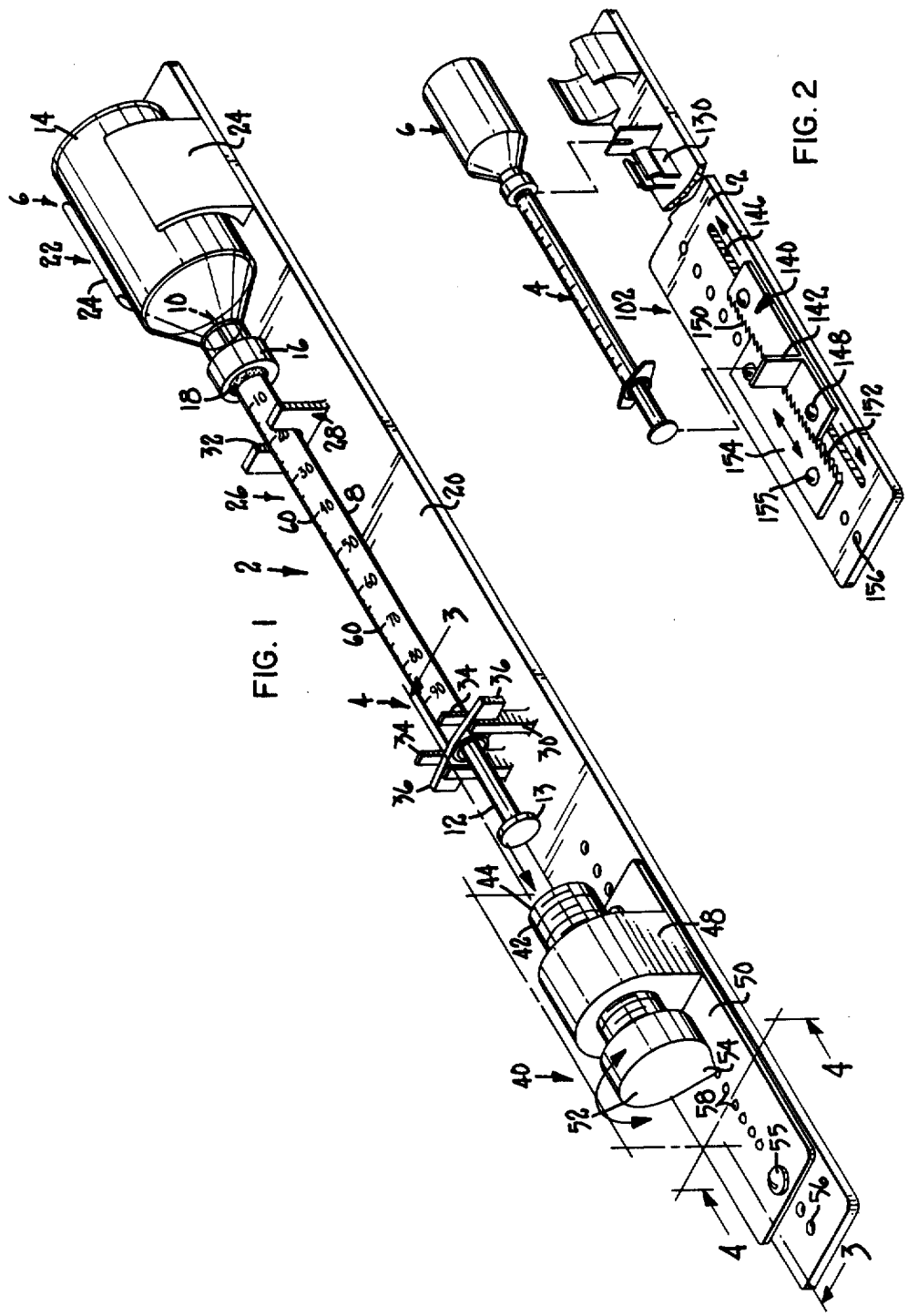

DOSAGE DEVICE

TECHNICAL FIELD

The present invention relates generally to a dosage device for allowing a hypodermic syringe to withdraw a predetermined dose of medication from a container thereof. As such this invention relates to the medical field and, particularly, to medical instruments used for the injection of medication.

DESCRIPTION OF THE PRIOR ART

Many people who are ill or who have certain diseases have to inject medication into themselves on a fairly regular basis. Diabetics are a good example. They have to inject insulin into themselves, usually on a daily basis, if they are to survive. Diabetics customarily administer their daily injections to themselves. It would be too expensive, or too much trouble, for the diabetic to go on a daily basis to a health care facility simply to have someone else administer the injection.

Unfortunately, one of the more debilitating effects of diabetes is that it may lead to impaired eye sight and even to total blindness. A blind diabetic has much more difficulty in administering injections to himself. This difficulty arises not so much because of the actual injection, since this can be done effectively even by a blind person, but in seeing that the proper amount of insulin is placed into the hypodermic syringe. Thus, it is necessary for someone else to first fill the syringe. This destroys in large part the advantage of having the diabetic administer the injections to himself because another person is now required to fill the syringe.

Various devices have been proposed for causing a predetermined amount of medication to be drawn into a hypodermic syringe. Some of these devices have been designed specifically for use by blind persons to enable them to fill their own syringes. Generally, such devices include a holder for the container of medication and a holder for the syringe. These holders are located on a base plate so that the needle of the syringe extends into the container. An adjustable stop member is located in back of the syringe to abut the plunger at some point in its travel. The dosage is regulated by the amount that the plunger can be withdrawn from the syringe. How far the plunger travels before it strikes the stop member determines the dosage. U.S. Pat. Nos. 3,833,030 to Walbauer et al, 3,840,011 to Wright, and 4,073,321 to Moskowitz disclose typical examples of such devices.

While the above-noted devices allow blind people to fill a syringe with a predetetermined dose of medication, the dosage level of the medication must first be set by a sighted person. In other words, the position of the adjustable stop member on the base plate, which controls the dosage size, must first be adjusted by a sighted person before the blind user can operate the device. There is no provision in these known devices for allowing the blind person to himself adjust or change the dosage level. Whenever a change in the dosage level is required, the assistance of a sighted person is again needed. This is burdensome to the blind patient, especially when changes in the dosage level are frequent.

SUMMARY OF THE INVENTION

One aspect of this invention relates to an improved dosage device for allowing a predetermined dose of medication to be inserted into a syringe from a container thereof. More particularly, the dosage device of this invention allows a visually impaired or blind person to change the dosage level without the aid of a sighted person. This obviates the major disadvantage of prior art devices.

The dosage device of this invention is designed for use with a container of medicine and a hypodermic syringe having a needle and an adjustable plunger. The dosage device includes a body having a holder for holding the medication container. A holder for the syringe is also provided on the body with the syringe having its needle extending into the container. An adjustable stop member is located in back of the plunger of the syringe for abutting the plunger to regulate the amount that the plunger can be withdrawn from the syringe. In addition, the dosage device includes means for indicating the position of the stop member to a visually impaired person. This position indicating means can have two forms. It may comprise means for generating an audible signal to the visually impaired person as the stop member moves through one of a plurality of discrete positions. This enables the user to count the audible signals to appropriately change the dosage level. Alternatively, the position indicating means may comprise means for generating a sensible pulse whenever the plunger passes through one of its discrete positions. These pulses may be felt by the patient in the same manner as the audible signals are heard in terms of adjusting the dosage level.

BRIEF DESCRIPTION OF THE DRAWINGS

This invention will be described hereafter in the Detailed Description, when taken in conjunction with the following drawings, in which like reference numerals refer to like elements throughout.

FIG. 1 is a perspective view of an improved dosage device according to a first embodiment of this invention;

FIG. 2 is a perspective view of an improved dosage device according to a second embodiment of this invention;

DETAILED DESCRIPTION

Figure 3:
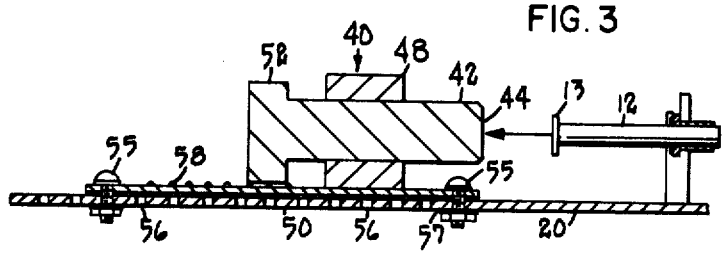
FIG. 3 is a partial cross-sectional view of the improved dosage device shown in FIG. 1, taken along lines 3—3 in FIG. 1.

Referring now to FIG. 1, a first embodiment of an improved dosage device according to this invention is generally illustrated as 2. Dosage device 2 is used for filling a hypodermic syringe 4 with a predetermined dose of medication normally contained in a container or vial 6. Hypodermic syringe 4 may be any conventional syringe or similar device having a cylindrical body 8, an outwardly protruding needle 10, and a movable plunger or piston 12 having an enlarged head 13. Whenever plunger 12 is withdrawn from body 8 (to the left in FIG. 1), a partial vacuum is produced inside the syringe which draws medication through the needle 10 and into body 8. When plunger 12 is pushed back through body 8, the reverse occurs and the medication will be dispensed out through needle 10. Container 6 may be any type of container which holds a suitable medication therein. The container shown in the drawings has a cylindrical body 14 and an outer cap 16 closed by a suitable plug 18. Needle 10 of syringe 4 is adapted to penetrate the plug 18 of cap 16 to extend inwardly into container 6. While the dosage device 2 of this invention is meant for use with syringe 4 in its container 6, neither the syringe nor the container form a part of dosage device 2 itself.

Dosage device 2 includes an elongated body 20. Body 20 is formed as a rectangular plate made from any suitable material. A holder 22 formed by two opposed spring arms 24 is located at one end of body 20. Spring arms 24 clamp the cylindrical body 14 of container 6 between them to fix container 6 on body 20. However, spring arms 24 can be flexed apart to allow container 6 to be removed and replaced as necessary.

In addition to holder 22, the body 20 contains a second holder, generally indicated as 26, for fixing the position of syringe 4 on body 20. Holder 26 comprises two spaced cradles 28 and 30. Cradle 28 has an upwardly facing U-shaped opening 30 which receives the cylindrical body 8 of syringe 4. Cradle 30 includes two sets of spaced arms which define two Y-shaped forks 34. A tab 36 which extends outwardly from each side of body 8 is received in one of the forks 34. Thus, the body 8 of syringe 4 is longitudinally constrained on the body 20 by virtue of holder 26. As shown in FIG. 1, the syringe 4 is adapted to be held by holder 26 in such a position that the needle 10 protrudes into the interior of container 6. Plunger 12 of syringe 4 is freely movable in body 8 even when syringe 4 is received in holder 26.

Figure 4:
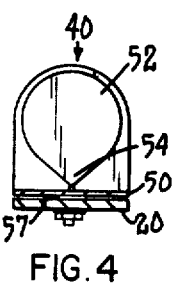
FIG. 4 is a cross-sectional view of the improved dosage device shown in FIG. 1, taken along lines 4—4 of FIG. 1.

Referring now to FIGS. 1, 3 and 4, dosage device 2 incudes a stop means, generally indicated as 40, for limiting the outward movement of plunger 12 as it is withdrawn from syringe 4. The stop means 40 includes an elongated stop member 42 having a first end 44 which serves as a stop surface for the head 13 of plunger 12. The stop member 42 is formed as a circular rod which is externally threaded to be rotatably received inside a threaded bearing block 48. Bearing block 48 is fixed to a base plate 50. In addition, the other end of stop member 42 has an enlarged head 52. Head 52 contains a protrusion or finger 54 which extends outwardly from the periphery thereof. As shown in FIG. 4, protrusion 54 is formed integrally with the head 52 so that the head 52 has a tear-drop shape. However, head 52 could be circular with protrusion 54 being formed by an outwardly extending flange or the like.

Base plate 50 of the stop means 40 is normally fixed to body 20 by means of two bolts 55. Bolts 55 pass downwardly through two selected apertures 56 contained in a line of such apertures on body 20. The use of a plurality of apertures 56 allows base plate 50 to be set into a position on the body 20 which is suitable for the length of syringe 4 used in dosage device 2. For example, if a relatively long syringe 4 is used, then the stop means 40 would be placed nearer the end of the body 20 then when a short syringe 4 is used. However, precise control of the position of stop member 42 is achieved by suitable rotation of the stop member 42 in bearing block 48. In other words, during normal operation of the dosage device 2, base plate 50 will always be fixed in a preselected position on body 20 which position has been selected such that the stop means 40 is located suitably in back of the head 13 of plunger 12. Whatever adjustments are then needed in terms of operating dosage device 2, which will be explained hereinafter, is achieved by rotation of the stop member 42 relative to base plate 50.

An important feature of dosage device 2 is that it includes means for indicating to a visually impaired or blind person the position of the stop member 42 on the body 20. In the FIG. 1 embodiment, this position indicating means comprises means for generating an audible signal each time stop member 42 passes through one of a plurality of discrete positions. This audible signal generating means preferably includes the protrusion 54 on head 52 and the linear series of raised lands or shoulders 58. The lands 58 are located on base plate 50 generally in line with the axis of stop member 42. Lands 58 are located beneath head 52 so as to normally interfere with protrusion 54 whenever the protrusion 54 attempts to pass over the lands. However, stop member 42 can be rotated so that the protrusion 54 passes over the land 58 with an audible click. For example, this can be accomplished simply by designing enough play into the stop member 42 so that the stop member can pass the protrusion 54 over the lands 58 after the initial engagement. Alternatively, base plate 50 may be made somewhat resilient by interposing washers 57 between base plate 50 and body 20. This resilience allows the protrusion 54 to contact, but yet pass over, each of the lands 58 with an audible click. Instead of a plurality of discrete lands 58, a longitudinally elongated raised ridge could be used on base plate 50.

Thus, dosage device 2 is advantageous because of the means for generating a series of audible clicks as the stop member 42 is moved through a plurality of discrete positions. The dimensions of stop member 42 (i.e., its diameter) are selected so that the stop member is moved on body 2 through a distance corresponding to one of the gradations 60 on the syringe for each 360° of rotation. However, each 360° of rotation also corresponds to one audible click generated by protrusion 54. Thus, each audible click in a series of clicks corresponds to the movement of stop member 42 through a distance equal to one of the gradations 60 on the syringe 4. The gradations 60 are a purely conventional marking located on the body 8 of the syringe which can be visually read as an indication of the dosage level of the medication in syringe 4. Although it is preferred that the dosage device 2 be calibrated so that 360° of rotation be equal to one of the gradations on syringe 4, the dosage device could be adjusted so that a lesser amount of rotation would be equal to one gradation. In such a case, the head 52 would preferably be formed with a plurality of protrusions 54 each of which would generate an audible click after the appropriate amount of rotation of head 52 for indicating that a distance equal to one gradation on the syringe has been reached.

Dosage device 2 allows a blind or visually impaired person to not only fill the syringe 4 himself each time an injection is required, but to adjust the dosage level as necessary. For example, assuming that stop member 42 is pre-set at a suitable position, all that is required for the blind person to do to fill the syringe is to draw plunger 12 back until it engages the stop member 42. This fills syringe 4 with a predetermined dose of the medication which is dependent on the position of stop member 42. However, now assume that the dosage level is to be increased by two gradations 60 on the syringe 4. Then it is only necessary for the blind person to manually rotate stop member 42 in the proper direction through two audible clicks which correspond to two complete rotations of the stop member 42. These two complete rotations have moved the stop member 42 back away from plunger 12 by a distance corresponding to two additional gradations 60 on the syringe 4. Thus, the blind person has effectively increased the dosage level two units without having need to resort to the aid of a sighted person. Similarly, the dosage level can be decreased as necessary simply by rotating the stop member 42 in the reverse direction.

Dosage device 2 according to this invention is particularly advantageous. It allows a blind or visually impaired person to give himself whatever injections are needed without the aid of a sighted person. It also allows the blind person to vary the dosage level of the injection according to a doctor's orders or according to a pre-set formula. It does so by including means which indicate to the blind person the position of the stop member 42 for the syringe plunger 12. Thus, dosage device 2 gives a blind or visually impaired person more freedom and confidence in administering to his own health needs. Dosage device 2 as disclosed herein is intended for use with diabetic patients who are also blind. However, dosage device 2 is not limited for use by diabetics, but could be used by any blind or visually impaired person for the filling of a syringe to be used in injecting any suitable medication.

Figure 5:
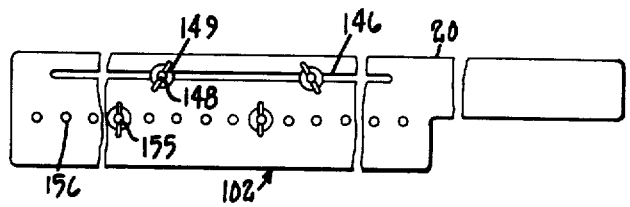
FIG. 5 is a bottom plan view of the improved dosage device shown in FIG. 2.
Figure 6:
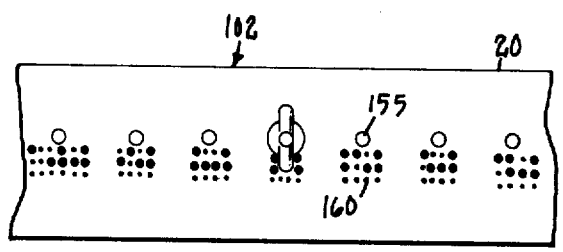
FIG. 6 is an enlarged bottom plan view of a portion of the improved dosage device shown in FIG. 2.

Referring now to FIGS. 2, 5, and 6, a second embodiment of the invention is indicated herein as 102. Those components of dosage device 102 which are similar to the components shown in the first embodiment will be identified with the same reference numerals used in FIGS. 1–3. Thus, dosage device 102 includes a body 20, a holder 26 for holding syringe 4, and a holder 22 for container 6. The holders 22 and 26 may be identical to or different from their counterparts in FIG. 1. For example, the cradle 30 in FIG. 1 has been replaced by a spring type clamp 130 in FIG. 2 even though the remaining components of the holders 22 and 26 are identical in both embodiments.

Dosage device 102 includes a different stop means for plunger 12 which stop means is generally indicated herein as 140. Stop means 140 includes an upwardly protruding stop member 142 against which the head 13 of plunger 12 is meant to abut. Stop member 142 is not, however, rotatable, but is instead slidably mounted on the body 20. Stop member 142 is formed as an integral part of a base plate or slide 144 which overlies an elongated slot 146 in body 20. Two downwardly projecting bolts 148 extend from base plate 144 through the slot 146. Wing nuts 149 are contained on the lower ends of the bolts 149 to releasably fix the position of stop member 142 relative to slot 146. Whenever it is desired to adjust the position of stop member 142 in slot 146, the wing nuts 149 are loosened and the user can grasp the top end of the stop member 142 with his hand and manually slide the stop member relative to the slide. When a new position is reached, wing nuts 149 are retightened.

One side of base plate 144 includes a toothed rack defined by a series of outwardly extending teeth 150. Teeth 150 cooperate with the teeth 152 of a second toothed rack 154. Rack 154 is fixedly mounted on body 20 adjacent that side of base plate 144 which contains teeth 150. The position of rack 154 can be adjusted on body 20 by virtue of two bolts 155 which can be positioned in any two of selected apertures 156 in a line of such apertures. Apertures 156 are similar to the apertures 56 in the embodiment of FIG. 1. However, for any given position of the rack 154, the rack 154 is stationary relative to the body 20 and the stop member 142 movable relative thereto.

The principles of operation behind the dosage device 122 are similar to those of dosage device 2. In other words, by varying the position of the stop member 142, the dose of medication which is drawn into the syringe 4 can be effectively changed. However, the position indicating means of the dosage device 102 is different from the FIG. 1 embodiment. Rather than relying on a series of audible clicks to indicate when the stop member passes through a series of discrete positions, instead the stop member 142 includes means for generating a sensible pulse as it passes through each position. These pulses are generated by the coaction of the teeth 150 and 152 as they move out of mesh and then back into mesh. These pulses can be sensed or felt with the hand of the blind person who is grasping the stop member 142 to slide the stop member. By feeling the number of pulses which is generated each time the teeth of one rack move another notch relative to the other rack, the blind person is able to know how far the stop member 142 has been moved on body 20. When the pulse generating means is calibrated to the syringe gradations 60, by counting the number of pulses, the blind person can himself effectively adjust the dosage level without the aid of a sighted person.

Both the stop means 140 and 40 include means for roughly adjusting the position thereof on body 20 relative to the syringe 4. See apertures 156 and 56. After that, the precise position of the stop member is controlled either by rotation of the stop member 42 as in FIG. 1, or by a sliding movement of the stop member 142 as in FIG. 2. However, the use of a gross adjustment of stop means 40 enables the dosage devices 2 and 102 to be used with syringes of greatly varying lengths. This is also a desirable feature and adds to the utility and versatility of this device.

In addition, reference markings in Braille characters may be added to the dosage device 2 and 102 if desired. For example, each of the lands 58 could have a Braille character placed next to it for indicating the dosage level in syringe 4 whenever the finger 54 is in contact with that particular land just prior to producing the audible click. As shown in FIG. 6, each of the holes 155 could have a Braille character 160 located next to it. Spacing between the holes 155 could correspond to ten gradations on the scale. An approximate idea of the dosage level in syringe 4 could then be obtained by means of a pointer or the like on the underside of the stop member 142. This pointer could have its position felt in relation to the hole 155 to determine an approximate dosage level inside syringe 4.

Various modifications of this invention will be apparent to those skilled in the art. For example, any suitable means for indicating the position of the stop member to a visually impaired person would be suitable. The embodiments of FIGS. 1 and 2 only disclose two such means. Thus, the scope of this invention is to be limited only by the appended claims.

I claim:

1. An improved dosage device for allowing a predetermined dose of a first substance to be withdrawn from a container thereof by a syringe having a needle and a movable plunger for drawing the first substance into the syringe, of the type which includes a body, means for holding the container of the first substance on the body, means for holding the syringe on the body in a spaced relation to the container with the needle thereof insertrating into the container; and stop means carried on the body in a spaced relation behind the syringe for abutting against the plunger to regulate the amount that the plunger can be withdrawn from the syringe, the stop means being movable on the body so that the dose of the first substance withdrawn from the container can be varied, and wherein the improvement comprises:

means for indicating the position of the stop means on the body to a visually impaired person who is thus enabled to adjust the position of the stop means without the aid of a sighted person to change the predetermined dose; in which the position indicating means comprises means for generating an audible signal at various discrete positions of the stop means, wherein the visually impaired person may adjust the position of the stop means to another desired position by counting the audible signals generated during movement of the stop means, wherein the audible signal generating means comprises:

(a) a base plate carried on the body;

(b) a rotatable stop member that defines the stop means, wherein the stop member is carried on the base plate and the position of the stop member is adjusted relative to the plunger by rotation thereof, the stop member having at least one outwardly extending protrusion;

(c) a portion of the base plate configured to coact with the protrusion on the stop member for generating the audible signal each time the stop member completes a predetermined arc of rotation; and (d) wherein the base plate is movable relative to the body and includes means for fixing the base plate to the body in different positions relative to the plunger of the syringe, whereby a gross adjustment of the stop means relative to the syringe to accommodate differently sized syringes is achieved by moving the base plate on the body and a fine adjustment of the stop means relative to the syringe is achieved by rotation of the stop member on the base plate.

2. An improved dosage device for allowing a predetermined dose of a first substance to be withdrawn from a container thereof by a syringe having a needle and a movable plunger for drawing the first substance into the syringe, of the type which includes a body; means for holding the container of the first substance on the body; means for holding the syringe on the body in a spaced relation to the container with the needle thereof penetrating into the container; and stop means carried on the body in a spaced relation behind the syringe for abutting against the plunger to regulate the amount that the plunger can be withdrawn from the syringe, the stop means being movable on the body so that the dose of the first substance withdrawn from the container can be varied; and wherein the improvement comprises:

means for indicating the position of the stop means on the body to a visually impaired person who is thus enabled to adjust the position of the stop means without the aid of a sighted person to change the predetermined dose, in which the position indicating means comprises means for generating an audible signal at various discrete positions of the stop means, wherein the visually impaired person may adjust the position of the stop means to another desired position by counting the audible signals generated during movement of the stop means, wherein the audible signal generating means comprises:

(a) a rotatable stop member that defines the stop means, wherein the stop member is carried on the body and the position of the stop member is adjusted relative to the plunger by rotation thereof, the stop member further having at least one outwardly extending protrusion;

(b) a portion of the body configured to coact with the protrusion on the stop member for generating the audible signal each time the stop member completes a predetermined arc of rotation, in which the portion of the body comprises a linear raised ridge thereon which is positioned to contact the protrusion of the stop member during rotation thereof, the raised ridge being resilient to allow the protrusion to pass thereover with an audible click; and (c) wherein the stop member carries only one outwardly extending protrusion for generating the audible signal after successive 360° increments of rotation, and wherein the stop member is calibrated to the syringe such that each 360° increment of rotation represents a discrete unit of dose in the syringe.

3. An improved dosage device for allowing a predetermined dose of a first substance to be withdrawn from a container thereof by a syringe having a needle and a movable plunger for drawing the first substance into the syringe, of the type which includes a body; means for holding the container of the first substance on the body; means for the holding the syringe on the body in a spaced relation to the container with the needle thereof penetrating into the container; and the stop means carried on the body in a spaced relation behind the syringe for abutting against the plunger to regulate the amount that the plunger can be withdrawn from the syringe, the stop means being movable on the body so that the dose of the first substance withdrawn from the container can be varied; and wherein the improvement comprises:

means for indicating the position of the stop means on the body to a visually impaired person who is thus enabled to adjust the position of the stop means without the aid of a sighted person to change the predetermined dose, in which the position indicating means comprises means for generating a sensible pulse in the stop means at various discrete positions thereof, whereby the visually impaired person may adjust the position of the stop means to another desired position by feeling and counting the pulses generated during movement of the stop means, wherein the pulse generating means comprises:

(a) an outwardly extending toothed rack that is part of the stop means, wherein the stop means is slidably mounted on the body;

(b) means located on the body for coacting with the teeth of the rack for generating the pulse each time the stop means is moved through one of its discrete positions, in which the coacting means comprises a second toothed rack fixedly carried on the body adjacent the stop means for coacting with the teeth of the rack on the stop means; and (c) wherein the stop means includes a handle which the visually impaired person holds during adjustment of the stop means, and wherein the pulse is communicated to the hand of the person through the handle.

* * * * *